July 5, 1938. J. A. HEIDBRINK Re. 20,781

GAS ADMINISTERING MACHINE

Original Filed Aug. 23, 1935 3 Sheets-Sheet 1

Inventor:
Jay A. Heidbrink.
By Whiteley and Ruckman
Attorneys

July 5, 1938. J. A. HEIDBRINK Re. 20,781

GAS ADMINISTERING MACHINE

Original Filed Aug. 23, 1935 3 Sheets-Sheet 2

Inventor:
Jay A. Heidbrink.
By Whiteley and Ruckman
Attorneys.

July 5, 1938. J. A. HEIDBRINK Re. 20,781
GAS ADMINISTERING MACHINE
Original Filed Aug. 23, 1935 3 Sheets-Sheet 3
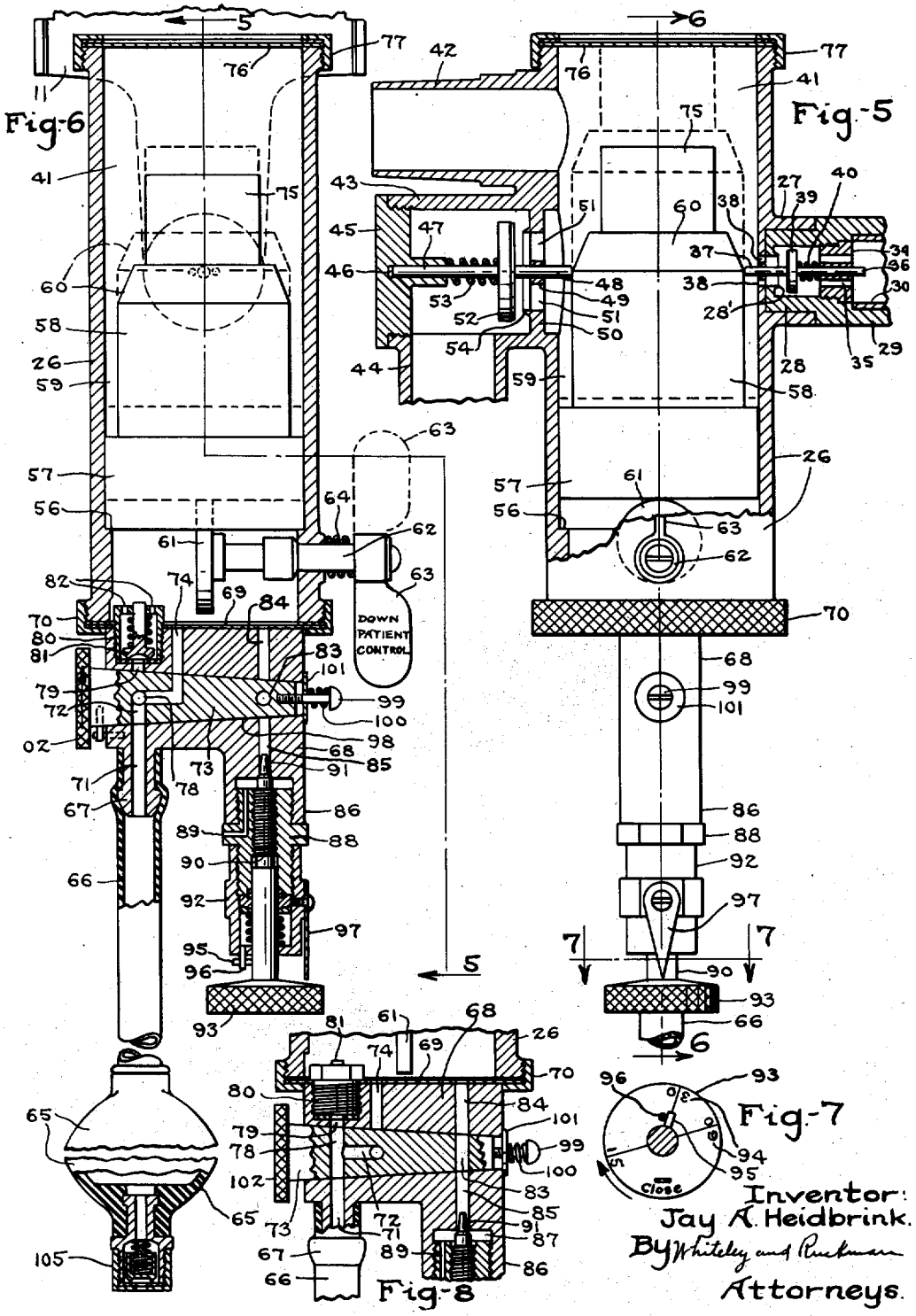

Reissued July 5, 1938

Re. 20,781

UNITED STATES PATENT OFFICE 20,781

GAS ADMINISTERING MACHINE

Jay A. Heidbrink, Minneapolis, Minn., assignor to The Ohio Chemical and Manufacturing Company, Cleveland, Ohio Original No. 2,100,778, dated November 30, 1937, Serial No. 37,498, August 23, 1935. Application for reissue January 26, 1938, Serial No. 187,057

11 Claims. (Cl. 128—203)

Figure 1:
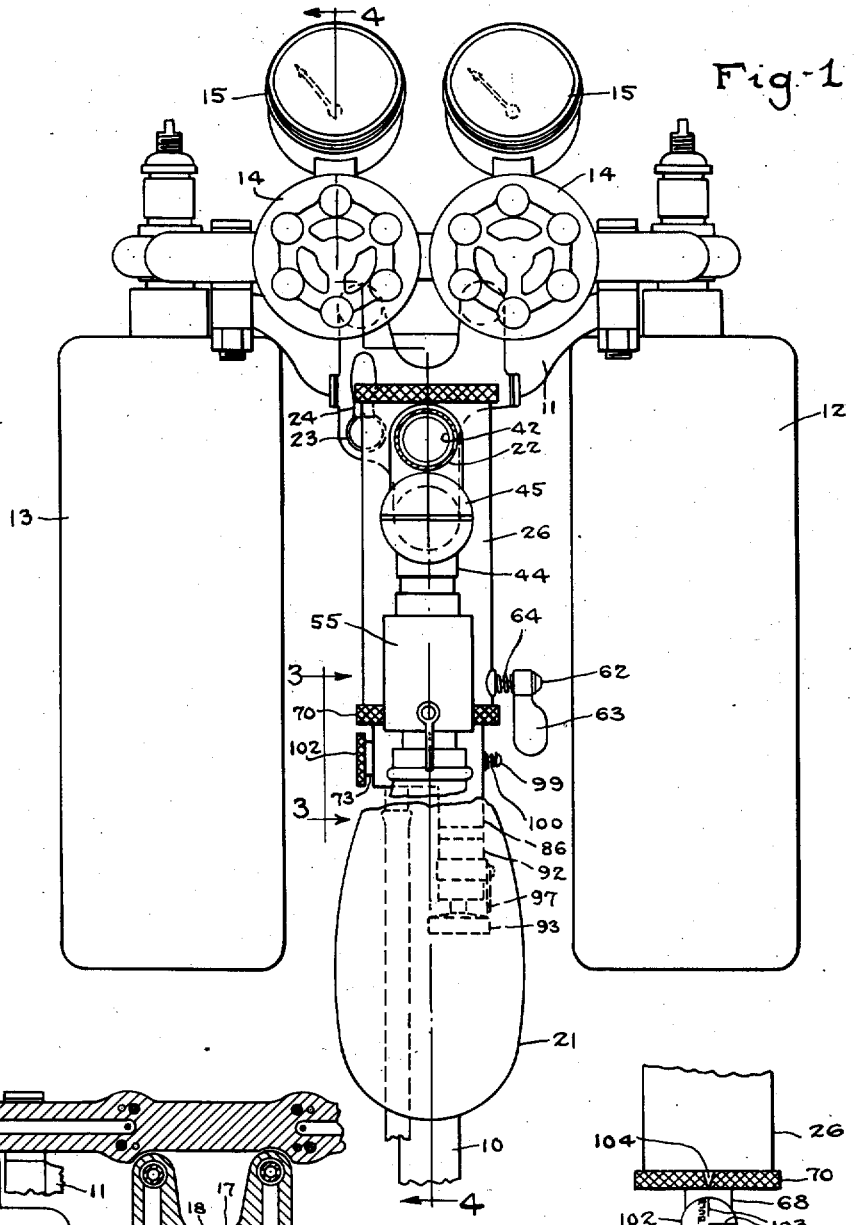

My invention relates to gas administering machines and has for its object to provide a machine for administering fluid for inhalation for producing varying states of anaesthesia, particularly that low form of anaesthesia known as analgesia, wherein the patient is conscious but the nerves are numbed and deadened to the sense of pain.

In many conditions of patients, such, for example, as that accompanying certain kinds of operations of dentists, or even in labor in child bearing, it is desirable to maintain the patient in a state of analgesia wherein the patient is only partly anaesthetized.

It is a principal purpose of my invention to provide means to permit the patient himself to control the flow and delivery of anaesthetizing fluid to himself, this control being customarily exercised in response to increased pain stimuli. The nature of the anaesthetizing fluid and its volume will be determined in advance by the operator. The anaesthetizing fluid may be any gas or mixture of gases customarily employed to produce anaesthesia, as nitrous oxide, or nitrous oxide mixed with air or oxygen.

It is a further object of my invention so to construct the patient-operated means, after operation by the patient to deliver gas to him automatically, as to cut off the delivery of gas so the patient cannot of his own will and initiative maintain a constant supply of gas, but can only secure supplies of gas intermittently.

It is a further object of my invention to provide means such that, when the patient operates the means which he supposes will cause delivery of gas to him, whether it does or not, there will be an indication to him, in the form shown and described, a sharp clicking noise, showing that he has operated the gas delivering means.

It is a further object of my invention to provide means such that after the patient has operated the gas control valves to cause delivery of anaesthetizing fluid to him, the machine will continue to deliver such fluid for definitely-timed periods under the control of the anaesthetist operator, at the ends of which periods supply of gas will be cut off.

It has been found in many cases that more favorable results are obtained by a constant flow of gas to the patient, determined by the trained anaesthetist. Yet, under such conditions, there may be surges of pain stimuli which will make the patient feel that he should have a larger supply of anaesthetizing gas, and might have his nervous tension increased if he though he wasn't getting it. It is an object of my invention to provide means whereby the patient can operate the machine to admit and cut off flow of gas for analgesia together with means whereby the operator can render the patient controlled means inoperative to cut off flow although still capable of being operated by the patient, so that the patient while receiving a constant flow of the gas as determined by the anaesthetist nevertheless believes that he is controlling the flow of gas with a highly valuable psychological effect on the patient.

The full objects and advantages of my invention will appear in connection with the detailed description thereof, and the novel features are particularly pointed out in the claims.

In the drawings, illustrating an application of my invention in one form,—

Figure 2:
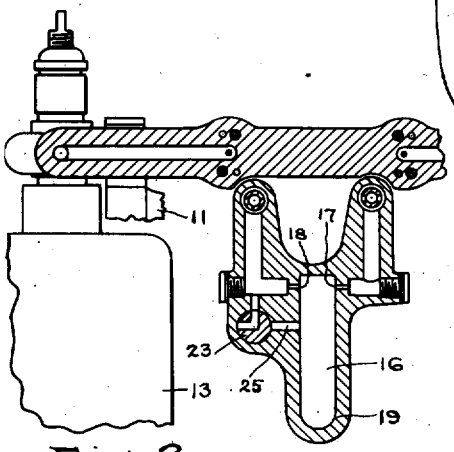
Figure 3:
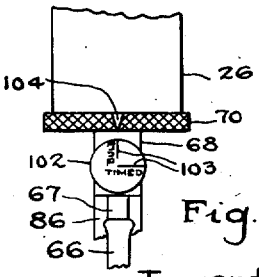
Figure 4:
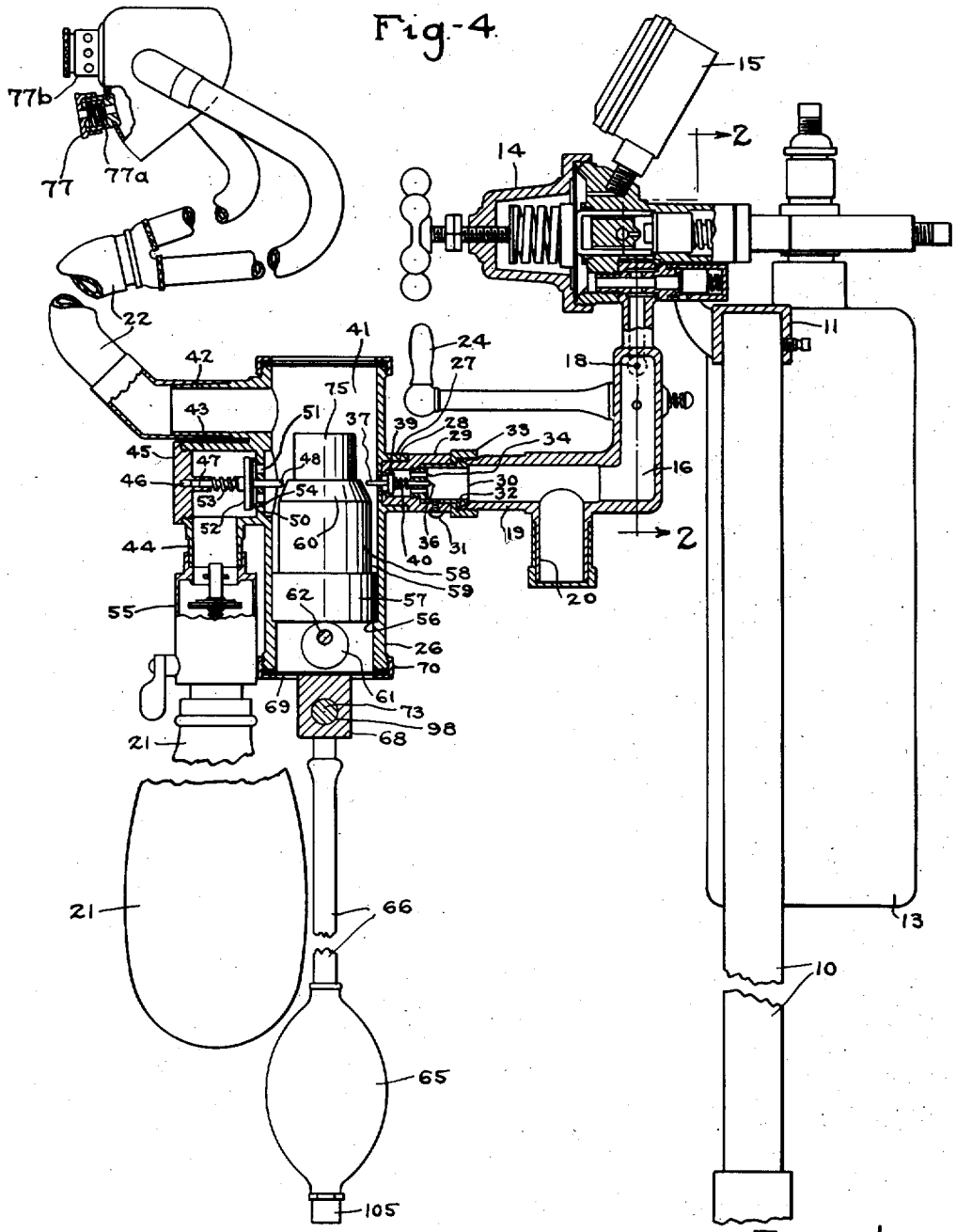

Fig. 1 is a front elevation view of an anaesthetizing machine embodying my invention. Fig. 2 is a sectional view taken on line 2—2 of Fig. 4. Fig. 3 is a fragmentary elevation view taken in the position of line 3—3 of Fig. 1. Fig. 4 is a part sectional elevation view taken in the plane of line 4—4 of Fig. 1. Fig. 5 is a part sectional elevation view taken on line 5—5 of Fig. 6. Fig. 6 is a sectional elevation view taken on the line 6—6 of Fig. 5. Fig. 7 is a sectional view taken on line 7—7 of Fig. 5. Fig. 8 is an end view similar to a portion of what is shown in Fig. 6, with the valve member in a different position.

As illustrated, a pedestal 10 supports head 11 upon which is a plurality of gas cylinders 12, 13, as nitrous oxide and oxygen or other gases which it is desired to deliver for anaesthetizing purposes. The head carries pressure reducers 14 and gauges 15 for each gas by means of which any gas may be delivered to a chamber 16, all in a well-known manner which it is unnecessary to describe, it being sufficient to note that the separate gases enter the chamber 16 through individual ports 17 and 18, as shown in Fig. 2, and leave the chamber through an extension member 19 as clearly shown in Fig. 4. Customarily a nipple 20 connected with a rebreathing bag 21 and a breathing tube 22 has been connected to the member 19. A valve 23 operated by a handle 24 may be employed to shoot a strong volume of one gas, as oxygen, through a special port 25 as shown in Fig. 2, for resuscitation or other purposes.

The invention herein disclosed and claimed, and as shown, may be in the form of an attachment interposed in the breathing line represented by members 19 and 22, or it may be formed directly upon the extension 19, eliminating the old breathing bag connector 20. This attachment comprises a cylindrical casing 26. On the inlet side this is provided with a nipple seat 27 into which projects a valve head 28 having thereon a valve seat 28' as clearly shown in Figs. 4 and 5. The valve head 28 is an extension of a cylindrical member 29 which is secured to an interior tubular connector member 30, Figs. 4 and 5, by means of a screw or screws 31. Member 30 embodies an outwardly extended annular flange 32, Fig. 4, which is embraced by a nut 33 threaded on the extension member, by which means the parts are maintained assembled in the breathing line. A guide member 34 provided with gas passages 35, Fig. 5, is threaded into the member 28 and has a central aperture which guides the valve stem 36, which valve stem has an inwardly projected part 37 which passes through a corresponding aperture in the wall of cylinder 26 within valve seat 29 and is surrounded by gas holes 38. Upon the valve stem 36 is a valve disc 39 normally held in closing relation to valve seat 28' by a spring 40, as shown in Fig. 4. The opening of this valve is effected by thrusting the forwardly-extended portion 37 of the valve stem outwardly from within the chamber 41 formed in the cylindrical member 26. The cylinder 26 carries a nipple 42 adapted to be connected with the breathing tube 22 as shown in Fig. 4. Cylinder 26 also carries a second cylindrical extension 43 which is provided with a depending nipple 44 to which the rebreathing bag 21 is connected, as best shown in Fig. 4. The cylindrical extension member 43 is closed by a cap screw 45 which is provided with a centrally positioned guide socket 46 in which operates a valve stem 47. An extension 48 of valve stem 47 passes through a guide 49 formed in a partition 50 which, except for apertures 51, closes the interior of extension member 43 from the chamber 41 in the cylindrical member 26. A valve disc 52 on valve stem portions 47, 48 is caused by coil spring 53 normally to engage a valve seat 54 formed on the partition member 50, the valve stem 48 projecting into the chamber 41 in cylinder 26. A bag shut-off 55 is adapted to throw the rebreathing bag 21 out of operation when that is desirable.

As the parts are shown in Fig. 4, the valve members 39 and 52 are held closed. That is the normal position of the parts, and when they are so positioned no gas can pass through into gas tube 22 to the patient or to waste out-of-doors. To operate the valves 39 and 52, I seat a piston 57 upon an internal ledge or support 56 toward the bottom of chamber 41 in cylinder 26. This piston carries a plunger 58 of reduced diameter so as to leave an annular passageway 59 between it and the inner walls of the cylinder 26. At the upper end of the plunger portion 58 there is formed an inwardly diminishing portion which provides a conical cam surface 60 in position to engage the ends of plunger portions 37 and 48 and move them from the position shown in Fig. 4 to the position shown in Fig. 5. That is from gas-closing position of Fig. 4 to the gas-open position of Fig. 5, which latter results from the plunger extensions 37 and 48 riding along the cam surface 60 to the cylindrical surface of plunger extension 58. It follows that whenever the piston 57 and its attached plunger portion 58 is raised in the chamber 41 within cylinder 26 the valves 39 and 52 are moved to open and permit gas to flow from the chamber 16 into chamber 41 and from there into rebreathing bag 21, when the same is not closed by cut-off valve 55, respectively.

The anaesthetist operator may control piston 57 and plunger 58 by means of cam member 61 positioned in the bottom of chamber 41 within cylinder 26 and fast on stem 62 which is operated by finger lever 63, the parts being held in substantially gas-tight relation by means of spring 64. In the up-position of the finger lever 63, as shown in Fig. 5, cam member 61 has engaged the bottom of piston 57, lifting it to the position there shown wherein the valve stems 37 and 48 have ridden along the cam surface 60 to the outside of plunger cylinder 58. In this position the valve members 39 and 52 are rendered inoperative to close the valves, and gas passes through and to the rebreathing bag the same as if the attachment herein described were not employed. When, however, the finger lever 63 is in the down-position of Figs. 1, 4 and 6, valves 39 and 52 are held in their normal operative position and no gas can pass through.

In the last-recited position, piston 57 may be operated to carry plunger 58 to open the valves by a blast of air injected below the plunger 57 by means of air bulb 65 connected by an extension tubing 66 on a nipple 67 carried by a valve casing 68. As shown in Fig. 4, valve casing 68 is fast on a closure disc 69, which is held to close the lower end of chamber 41 within cylinder 26 by clamp nut 70. The nipple 67 has an aperture 71 which passes therethrough and into the valve piece 68, being adapted to register with an indirect or Z-passageway 72 within a valve member 73. This Z-passageway in turn registers with a second passageway 74 in the valve casing 68, which passageway opens through the closure disc 69 below the piston 57, all as clearly shown in Fig. 6. When the parts are in this position the blast of air injected under piston 57 by the closing of bulb 55 in the hands (of the patient or other operator) will rapidly lift piston 57 and parts carried thereby until the projection 75 thereon strikes the top disc 76, which, by means of clamp nut 77 is held to close the top of chamber 41 within cylinder 26, the position of the parts at such time being shown in dotted lines in Fig. 5. The striking of extension 75 upon disc 76 will produce a sharp clapping or clicking sound audible to the patient even though he may be some distance from the machine. This constitutes an indication to the patient that he has operated the valve-opening mechanism to permit anaesthetizing gas to flow to him. The patient is correctly advised that the valves are opened, because when piston 57 and connected parts rise to the dotted-line position of Fig. 5, the valves in fact are opened. When this is done, with valve 73 in the position of Fig. 6, if the patient releases bulb 65, as he will be instructed to do, the weight of piston 57 and connected parts will quickly restore them to the operative position of Fig. 6, the air injected by the blast going back through the various connections again into bulb 65.

Because, when the bulb is released and the piston 57 returned to normal position, the valves 39 and 52 close off both admission of fresh gas and entrance of the breathing line to the rebreathing bag, it is necessary for the patient to be provided with means of obtaining air for breathing. This is accomplished by means of an automatic inlet valve 77. This valve is always operative but the coil spring 77a against which the valve disk operates provides enough restriction so that when the valves 39 and 52 are open, the intake will be principally, if not entirely, from the breathing line including the fresh gas supply and the re-breathing bag. Ordinarily the exhaling valve 77b will be kept open and will remain open, it giving enough restriction to exhalation so that most or all of the exhaled gas will go to the re-breathing bag when that is open.

The patient may, when the parts are in the position of Fig. 6, maintain his grip on the bulb 65 to keep it closed. If that is done, there will be a continuation of a supply to the patient of anaesthetic. Even when the anaesthetist has instructed the patient to release the bulb so that he will receive only intermittent supplies of gas, pain stimuli may cause the patient not to follow instructions, but to continue to grip the bulb 65 with the intention of continuing to supply himself with anaesthetic. In either event, since there can be no escape of the air from below the piston 57 as long as the bulb 65 is held gripped, the piston could not descend and the patient would, in fact, continue to supply himself with anaesthetizing fluid. At times this might be ill advised and against the will and intent of the operating anaesthetist. Of course, if the cam member 61 has been lifted into the position of Fig. 5, so the valves are premanently held open, as intended by the anaesthetist, nothing will come from the patient's efforts. With the arrangement as in Fig. 5, the patient from time to time will squeeze the bulb and hear the sharp click or clap of the projection 75 upon closure disk 76, and will believe he is controlling the flow of anaesthetizing gas to himself, or that he is obtaining a continuous flow by his own act. In many cases this belief has an extremely beneficial effect upon the patient, so when the operator himself maintains the valves open to permit continuous flow of anaesthetic as controlled by the operator, he will leave the valve 73 in the position of Fig. 6, and encourage the patient to operate the bulb 65 and encourage the patient to believe that he himself is controlling the administration of anaesthetic.

When, however, it is not desirable to have continuous flow of anaesthetic to the patient, and when it is desirable that the patient may not himself be able to secure continuous flow, though he may think he is securing it, the valve 73 is rotated to the position shown in Fig. 8. In this position a second passageway 78 in valve 73 leads directly to register with a passageway 79 in valve plug 68, which in turn leads through a casing 80 in which is a check valve 81. The casing 80 extends through the closure disc 69 and admits air under piston 57 through openings 82 in the casing 80. At the same time a third aperture 83 in valve member 73 registers with an aperture 84 extending through valve piece 68 and closure 69 which opens within the chamber 41 in cylinder 26. At its other end aperture 83 registers with an aperture 85 extending downwardly through an extension 86 of valve piece 68 into a chamber 87 therein. Chamber 87 is closed by extension nut 88 and has a discharge therefrom through passageway 89. Centrally threaded in the extension nut 88 is the stem 90 of a graduated needle valve 91 and the end of extension nut 88 is closed by a packing nut 92. Valve stem 90 has on the end thereof a knurled thumb nut 93 which is formed on its inside with a scale indicated at 94 in Fig. 7. On the stem is a pin 95 which is adapted to engage a stop pin 96 fast on the nut 92. And when these parts are in engagement as shown in Figs. 6 and 7, the needle valve is closed and a pointer 97 carried on the nut 92 will point on the scale to "close". When the needle valve is in that position and the bulb 65 has been operated to lift the piston 57 and connected parts to the dotted-line position of Fig. 5, no air can escape from beneath the cylinder 57, with the result that the parts will be held in that position and the valves 39 and 52 will be kept open to permit continuous flow of anaesthetizing gas to the breathing line. When the thumb nut 93 is revolved to the left, as indicated by the arrow in Fig. 7, the needle valve will be opened varying degrees, indicated on the scale as progressively decreasing periods of time, which will permit air to escape from below piston 57 so that it and the parts connected with it may descend. They will do this in periods of time inversely proportionate to the degree of openings, as indicated in Fig. 7. Thus, when the figure 60 is at the pointer it will take sixty seconds for the piston to descend and the valves to close. When the pointer points to "30" it will take thirty seconds. When it points to "15" it will take fifteen seconds. With this arrangement the operator or anaesthetist can provide that after each time the patient closes the bulb 65 he will have gas flowed to him for a definite period of time determined by the anaesthetist anywhere from one or two minutes down to a few seconds.

The valve 73 may conveniently be made cone-shaped, as clearly indicated in Fig. 6, and is held seated in a cone-shaped seat 98 by means of a screw 99 threaded into the end of valve block 73, there being a spring 100 between the screw head and a washerplate 101 to hold the valve firmly seated at all times. Upon the end of the valve 73 is a knurled thumb piece 102 upon which are scale lines 103, Fig. 3, indicating, on a pointer 104 on clamp nut 60, whether the valve is set for single direct transmission back and forth below the piston 57, or for timed expulsion of the air below it, and therefore, timed operation of the valves 39 and 52. An inlet check valve for bulb 65 is indicated at 105.

The advantages of my invention will be apparent from the foregoing description thereof. The operating anaesthetist controls, of course, the fluid for inhalation, and may control fully the volume going to the patient, even though the patient is led by the operation of the machine to think he is himself controlling the flow of gas which he is taking, with the psychological advantages which follow from that belief. The operator may, however, set the machine so the patient does himself control the flow of gas which he is getting, or he may so adjust the machine that the patient has control of the initial admission of gas to the patient, but the operating anaesthetist may determine how long the patient shall get a supply of anaesthetizing gas after each time he operates the delivery control mechanism. The arrangement is simple, not expensive to construct and in a high degree accurate and efficient.

I claim:

1. An anaesthetizing machine comprising a conduit for conducting anaesthetizing gas to the patient, valve mechanism in said conduit for normally blocking the flow of gas therethrough, means operative by the patient to open said valve mechanism to permit flow of gas to the patient, means to indicate such operation to the patient, and means under the control of the anaesthetist to position said patient-operated means so as to hold the valve mechanism open while said means is still capable of conscious operation by the patient and while the said indicating means is still operative.

2. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, and means controlled by the patient to effect operation of said piston.

3. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, means controlled by the patient to effect operation of said piston, and means operated by said piston to indicate to the patient that the piston has been operated.

4. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, means controlled by the patient to effect operation of said piston, and a striker on said piston engageable with the top of the cylinder chamber to make a distinctive sound when the piston is operated to indicate to the patient that the piston has been operated.

5. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, an air bulb adapted to be held in the hand of the operator, and an air conduit therefrom to below the piston whereby the patient may effect operation of said piston.

6. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, an air bulb adapted to be held in the hand of the operator, an air conduit therefrom to below the piston whereby the patient may effect operation of said piston, and a valve across said last-named conduit for controlling flow of air beneath the piston.

7. An anaesthetizing machine comprising a conduit for conducting anaesthetizing gas to the patient, a cylinder chamber in the conduit, valve mechanism associated with said chamber for normally blocking the flow of gas therethrough, a piston in said chamber having means thereon adapted to cooperate with said valve mechanism to open the same to permit flow of gas to the patient, an air bulb adapted to be held in the hand of the operator, an air conduit therefrom to below the piston whereby the patient may effect operation of said piston, and means under the control of the anaesthetizing operator to determine the length of time requisite for said air to exhaust from beneath the piston to permit the valve mechanism to close.

8. An anaesthetizing machine comprising a conduit for conducting anaesthetizing gas to the patient, a cylinder chamber in the conduit, valve mechanism including a valve stem projecting into said chamber for normally blocking the flow of gas therethrough, a piston in said chamber having means thereon adapted to engage said valve stem to open the valve to permit flow of gas to the patient, and means operated by the patient to force a blast of air under the piston to operate the same.

9. An anaesthetizing machine comprising a conduit for conducting anaesthetizing gas to the patient, a cylinder chamber in the conduit, valve mechanism including a valve stem projecting into said chamber for normally blocking the flow of gas therethrough, a piston in said chamber having means thereon adapted to engage said valve stem to open the valve to permit flow of gas to the patient, means operated by the patient to force a blast of air under the piston to operate the same, and means controlled by the anaesthetizing operator to release said air from beneath the piston in predetermined periods of time for permitting the piston to return to a position such that the valve may go into normal gas blocking position.

10. An anaesthetizing machine comprising a conduit for conducting anaesthetizing gas to the patient, a cylinder chamber in the conduit, a rebreathing bag connected with said cylinder chamber, valve mechanism associated with said chamber for normally blocking the flow of gas through the chamber and to the rebreathing bag, a piston in said chamber having means thereon adapted to cooperate with all said valve mechanism to open the same to permit flow of gas to the rebreathing bag and to the patient, and means controlled by the patient to effect operation of said piston.

11. An anaesthetizing machine comprising a conduit for conducting anaesthetizing gas to the patient, a cylinder chamber in the conduit, a rebreathing bag connected with said cylinder chamber, a valve for admitting gas into the chamber and another valve for admitting gas to the rebreathing bag, each of said valves including a valve stem projecting into said chamber for normally blocking the flow of gas thereinto and to the rebreathing bag, a piston in said chamber having means thereon adapted to engage said valve stems to open the valves to permit flow of gas to the rebreathing bag and to the patient, and means controlled by the patient to effect operation of said piston.

JAY A. HEIDBRINK.